(12) United States Patent
Cheetham

(10) Patent No.: US 8,584,838 B2
(45) Date of Patent: *Nov. 19, 2013

(54) CONTAINER FOR MIXING OF COMPONENTS

(75) Inventor: Joshua James Cheetham, Chicago, IL (US)

(73) Assignee: SDI (North America), Inc., Bensenville, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/873,139

(22) Filed: Aug. 31, 2010

(65) Prior Publication Data
US 2011/0056853 A1 Mar. 10, 2011

(30) Foreign Application Priority Data
Sep. 8, 2009 (AU) .................................. 2009904278

(51) Int. Cl.
*B65D 25/08* (2006.01)
(52) U.S. Cl.
USPC ............................. 206/219; 206/63.5; 433/90
(58) Field of Classification Search
USPC ........ 206/219, 222, 568, 221, 220, 63.5, 368; 433/90; 215/DIG. 8; 222/129, 136, 222/541.3, 541.4
See application file for complete search history.

(56) References Cited

U.S. PATENT DOCUMENTS

| | | | | |
|---|---|---|---|---|
| 3,684,136 A | * | 8/1972 | Baumann | 222/386 |
| 3,756,390 A | * | 9/1973 | Abbey et al. | 206/219 |
| 4,941,751 A | * | 7/1990 | Muhlbauer | 366/182.1 |
| 5,026,283 A | * | 6/1991 | Osanai et al. | 433/90 |
| 5,172,807 A | * | 12/1992 | Dragan et al. | 206/219 |
| 5,392,904 A | * | 2/1995 | Frick et al. | 206/219 |
| 6,386,872 B1 | * | 5/2002 | Mukasa et al. | 433/90 |
| 6,682,347 B2 | * | 1/2004 | Aoyagi et al. | 433/90 |
| 6,821,012 B2 | * | 11/2004 | Suzuki et al. | 366/139 |
| 6,869,284 B2 | * | 3/2005 | Aoyagi et al. | 433/90 |
| 2001/0052511 A1 | * | 12/2001 | Briand et al. | 219/61 |
| 2002/0098462 A1 | * | 7/2002 | Kaneko et al. | 433/89 |
| 2004/0020796 A1 | * | 2/2004 | Cheetham et al. | 206/63.5 |

FOREIGN PATENT DOCUMENTS

EP 1219262 A1 * 7/2002

* cited by examiner

*Primary Examiner* — Steven A. Reynolds
(74) *Attorney, Agent, or Firm* — William H. Holt

(57) ABSTRACT

A container (10) for mixing components, the container including a main body (12) defining a main chamber (17), a liquid receptacle (16), and a plunger (18). The main chamber has a distal end (26) which has an end cap (28). The main chamber also includes a central aperture (30) sealed by a frangible membrane (38). In use, the plunger causes liquid in the liquid receptacle to be pushed through an internal wall (22), having a weakened portion (24) therein, into the main chamber to mix the liquid with a powder contained in the main chamber. The liquid and powder are mixed to form a paste that is accessed by an applicator which is used to break the frangible membrane (38). The paste is preferably of the type used in dentistry.

8 Claims, 4 Drawing Sheets

CONTAINER FOR MIXING OF COMPONENTS

FIELD OF THE INVENTION

The present invention relates to a container for the mixing of components.

SUMMARY OF THE INVENTION

In accordance with one aspect of the present invention there is provided a container for mixing of components of a mixture, comprising a main chamber, a liquid receptacle and a plunger, the main chamber having an end wall which is frangible so as to provide access for an applicator device after mixing has been undertaken.

DESCRIPTION OF THE DRAWINGS

The present invention will now be described, by way of example, with reference to the accompanying drawings, in which.

DETAILED DESCRIPTION OF THE DRAWINGS

Figure 1:
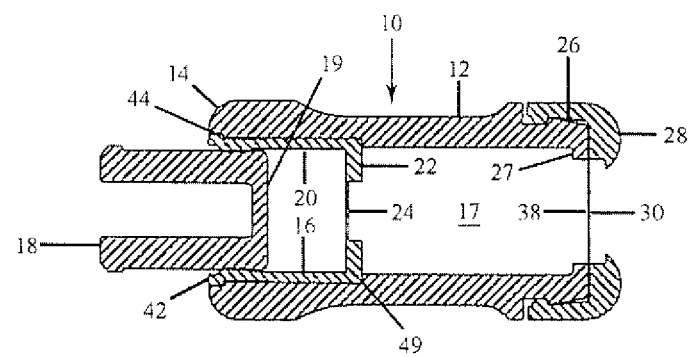
FIG. 1 is a sectional view of an empty container in accordance with the present invention in an initial condition.

Referring to FIG. 1 of the accompanying drawings, there is shown a container 10 for the mixing of two components. The container 10 comprises a body 12 which is cylindrical in section and has a main chamber 17. Mounted within a proximal end 14 of the body 12 is a liquid receptacle 16. A plunger 18 having a front face 19 is mounted within an interior of the liquid receptacle 16. The liquid receptacle 16 is sealed by the plunger 18 by seal means (not shown) located on the plunger 18 on an external face thereof or on an internal surface 20 of the liquid receptacle 16. The liquid receptacle 16 has an inner transverse wall 22 which contains a centrally disposed weakened portion 24.

Figure 3:
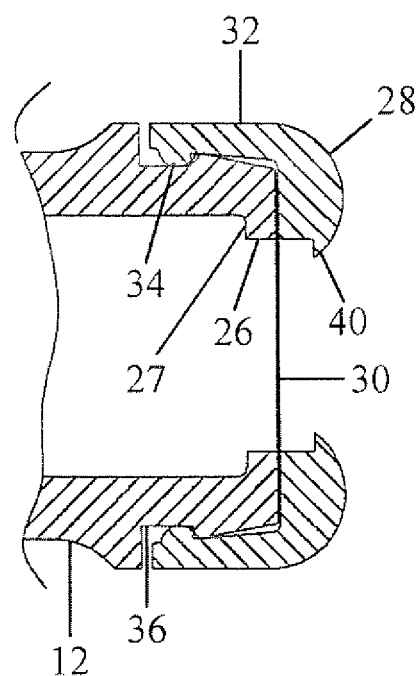
FIG. 3 is an enlarged section view of a distal end of the container of FIGS. 1 and 2.

A distal end 26 of the body 12 has an end cap 28 mounted thereto. Further, the distal end 26 is provided with an inwardly facing circumferential flange 27. The end cap 28 is annular and contains a central aperture 30. As shown in FIG. 3 the end cap 28 has a circumferential flange 32 which extends over the distal end 26. The flange 32 has an inwardly projecting annular rib 34 which engages with an external annular recess 36 in the body 12 adjacent the distal end 26. A thin frangible membrane 38 is mounted between the distal end 26 and the flange 27 and the end cap 28. The thin frangible membrane 38 may be retained in place by any convenient means such as adhesive. Further, the end cap 28 has an inwardly projecting annular lip 40 around the aperture 30. As can be seen in FIG. 1 the receptacle 16 has a rear laterally extending annular flange 42 which engages with an annular recess 44 on an internal face of the body 12 adjacent the proximal end 14 thereof.

Typically, the thin frangible membrane 38 is manufactured from a thin film or foil that is impermeable to moisture. For example, the thin frangible membrane 38 could be manufactured from an aluminium foil with a heat sealable adhesive on one side. After application of heat or energy (for example ultrasonic energy or induction energy or pressure) the adhesive layer bonds to the distal end 26 and cannot be readily removed. Other examples of the thin frangible membrane 38 are laminated aluminium and plastic films, where two or more films are joined together, and subsequently bonded to the distal end 26.

It is important that the underside of this membrane, which is in contact with the powder 48 (see FIGS. 4 and 5), is compatible with the powder 48 and will not participate in any chemical reaction with the powder. Thus, in the example where the membrane is aluminium foil with an adhesive coating on the underside; it is the adhesive layer that prevents any contact of the powder with the aluminium layer of the membrane.

Preferably the frangible membrane 38 is from 0.005 to 0.5 mm thick, more preferably from 0.01 to 0.3 mm thick.

Figure 2:
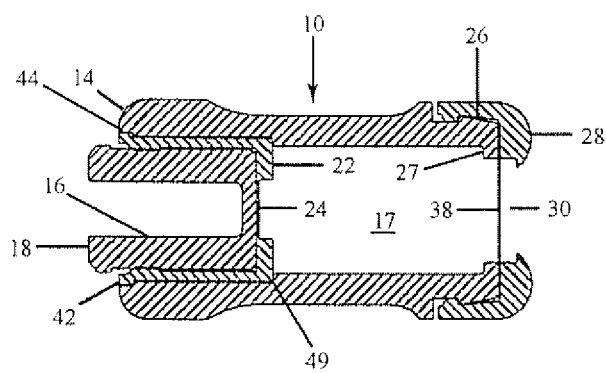
FIG. 2 is a sectional view of the container of FIG. 1 in an activated condition.

Referring to FIG. 2 there is shown the condition of the container 10 when activated. In this condition the plunger 18 has been depressed into the liquid receptacle 16.

When fully depressed a front face of the plunger 18 is engaged with the wall 22 of the liquid receptacle 16. Further forward displacement of the plunger 18 causes an increase in hydraulic pressure on the weakened portion 24. Once the hydraulic pressure reaches a critical point the portion 24 will break. This forces a liquid 46 (see FIGS. 4 and 5) from within the liquid receptacle 16 into the main chamber 17 to allow mixing with a powder 48 (see FIGS. 4 and 5). The engagement of the flange 42 with the recess 44 prevents the receptacle 16 from being pushed fully into the body 12. A further optional inwardly extending step 49 located on the body 12 may also be used to prevent the liquid receptacle 16 from being pushed into the body 12 (see to FIGS. 1 and 2).

Figure 4:
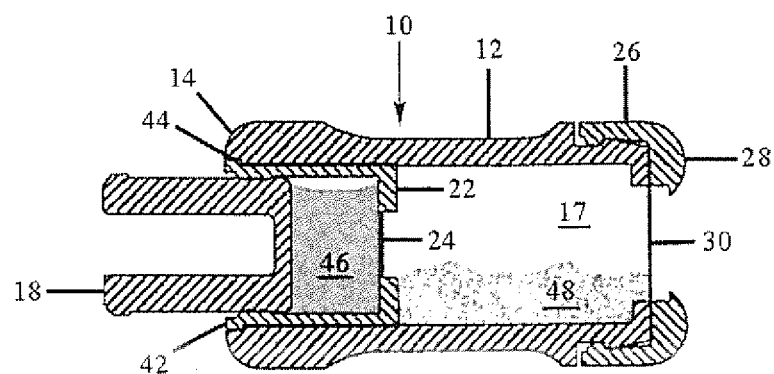
FIG. 4 is a sectional view of a further example of the container containing materials to be mixed in an initial condition.
Figure 5:
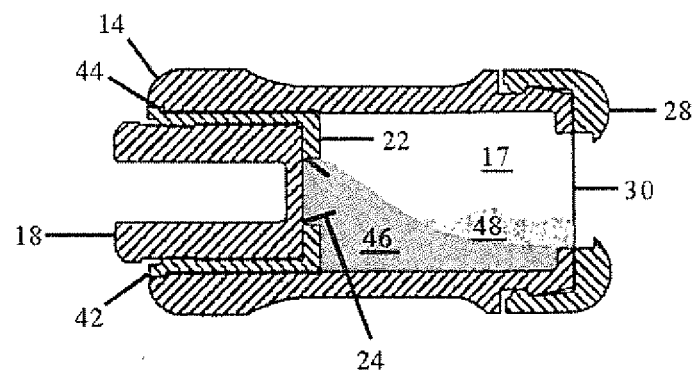
FIG. 5 is a sectional view of the loaded container of FIG. 4 in an activated condition ready to be placed into a mixing device.

In use, the powder 48 and the liquid 46 are loaded initially into the appropriate sections of the body 12 and the liquid receptacle 16 as shown in FIG. 4. The user then takes the container 10 and applies pressure to the plunger 18. Pressure applied to the plunger 18 builds hydraulic pressure against the portion 24 of the wall 22 through displacement of the liquid 46. Once the hydraulic pressure reaches a critical point the portion 24 will break. The user continues to apply pressure to the plunger 18 causing it to displace until the front face of the plunger engages with the wall 22 of the liquid receptacle 16. The liquid 46 is forced from the liquid receptacle 16 into the main chamber 17. The liquid 46 and the powder 48 are thus placed together within the main chamber 17 which forms a mixing compartment.

Figure 6:
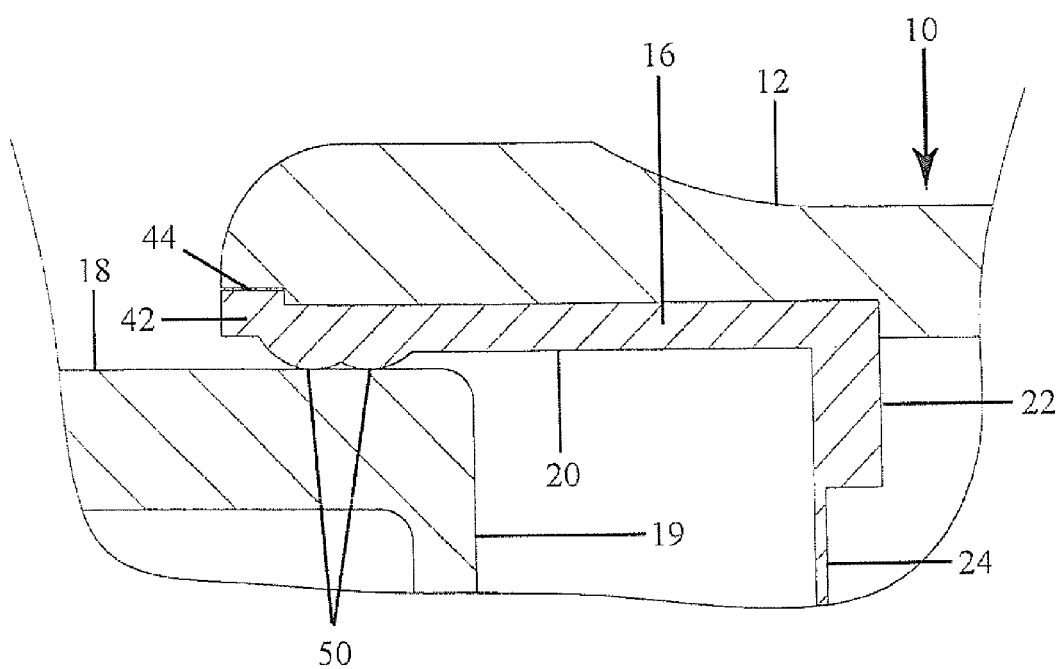
FIG. 6 is a partial sectional view of the container in accordance with the present invention showing a preferred sealing means.

In FIG. 6 of the accompanying drawings there is shown a preferred means for forming a seal between the plunger 18 and the receptacle 16. In this embodiment the inner wall 20 of the receptacle 16 is provided with a pair of spaced inwardly facing annular projections 50. This arrangement ensures that a good seal is maintained between the receptacle 16 and the plunger 18 when depressing the plunger 18 and forcing the liquid from the receptacle 16 into the chamber 17.

The container 10 is then placed into a mixer of a known type, for example a vibrating mixer. After sufficient mixing has occurred the liquid 46 and the powder 48 will form a paste.

to The user then takes the container 10 and forces an applicator with an absorbent end, or a brush, both commonly known, through the frangible membrane 38 causing the membrane 38 to puncture. The paste is then collected on the known applicator device for application by the user. To ensure excess paste is not removed the lip 40 is used to wipe excess material from the applicator without contamination.

The container of the present invention is particularly envisaged for use in mixing of dental materials but it is to be understood that it is of general applicability.

Modifications and variations as would be apparent to a skilled addressee are deemed to be within the scope of the present invention.

The invention claimed is:

1. A dental container for mixing of components of a dental mixture, comprising a main chamber, a liquid receptacle and a plunger, wherein said container further comprises a body having a proximal end and a distal end, said liquid receptacle being mounted within said proximal end of said body, and said plunger being sealingly mounted within an interior of said liquid receptacle, said liquid receptacle having an inner transverse wall which contains a weakened portion, and wherein said plunger has a front face which is projection free, said liquid receptacle containing a liquid and said main chamber containing a powder, the arrangement being such that, in use, pressure is applied to said plunger for building up hydraulic pressure by means of the liquid on said inner transverse wall for hydraulically breaking said weakened portion and for causing said liquid to enter said main chamber, said distal end of said body comprising an inwardly facing circumferential flange defining a central distal aperture, an end cap being mounted to said distal end of said body and having a circumferential configuration defining a central aperture substantially coterminous with said central distal aperture, a frangible membrane disposed across said central distal aperture of said body and said central aperture of said end cap by being sandwiched between said circumferential flange of said distal end of said body and said end cap, said body being devoid of any dispensing nozzle adjacent to said distal end thereof, wherein said frangible membrane is accessible to an applicator with an absorbent end or a brush held by a user after mixing has taken place whilst said end cap remains in place.

2. A dental container according to claim 1, wherein said end cap has a circumferential flange which extends over said distal end of said body.

3. A dental container according to claim 1, wherein said end cap has a circumferential flange which extends over said distal end of said body, and said flange on said end cap having an inwardly projecting annular rib engaged with an annular external recess in said body adjacent said distal end thereof.

4. A dental container according to claim 1, wherein said end cap has an inwardly projecting annular lip around said central aperture of said end cap.

5. A dental container according to claim 1, wherein said body has an inwardly extending step which engages with said liquid receptacle for preventing said liquid, receptacle from being pushed into said body.

6. A dental container according to claim 1, wherein said liquid receptacle has a rear outwardly extending annular flange in engagement with an annular recess on an internal face of said body adjacent said proximal end thereof for preventing said liquid receptacle from being pushed fully into said body.

7. A dental container according to claim 1, wherein said frangible membrane is from 0.005 to 0.5 mm thick.

8. A dental container according to claim 6, wherein said frangible membrane is from 0.01 to 0.3 mm thick.

* * * * *